(12) United States Patent
Kuo et al.

(10) Patent No.: US 6,183,972 B1
(45) Date of Patent: Feb. 6, 2001

(54) METHOD FOR THE DETERMINATION OF ANALYTE CONCENTRATION IN A LATERAL FLOW SANDWICH IMMUNOASSAY EXHIBITING HIGH-DOSE HOOK EFFECT

(75) Inventors: Hai-Hang Kuo, Granger; Lisa A. Meritt, Goshen, both of IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/122,736

(22) Filed: Jul. 27, 1998

(51) Int. Cl.[7] ............... G01N 33/544; G01N 33/577; G01N 33/53; G01N 33/537; C07K 16/44

(52) U.S. Cl. ................... 435/7.1; 435/4; 435/5; 435/6; 435/7; 435/7.1; 435/7.21; 435/7.92; 435/169; 435/810; 435/805; 435/970; 435/973; 435/975; 435/174; 435/517; 435/7.5; 435/7.93; 435/7.9; 435/7.94; 435/29; 435/960; 435/961; 435/240.27; 436/501; 436/514; 436/518; 436/523; 436/525; 436/538; 436/810; 436/169; 436/172; 436/542; 436/533; 436/164; 436/541

(58) Field of Search ................ 435/7.1, 287.2, 435/7.92, 169, 810, 805, 970; 436/523, 169, 525, 514, 810; 422/56, 63; 23/230 B (56) References Cited

U.S. PATENT DOCUMENTS 5,569,608 * 10/1996 Sommer ................ 436/518

OTHER PUBLICATIONS

Barbarakis et al., "Observation of Hook Effects in the Inhibition and Dose–Response Curves of Biotin Assays based on the Interaction of Biotinylated Glucose Oxidase with (Strep)avidin"., Analytical Chemistry, 1993, vol. 65., pp. 457–460.*
Rodbard et al., "Kinetics of two–site immunoradiometric ('sandwich') assays–I"., Immunochemistry, 1978, vol. 15, pp. 71–76.*
Rodbard et al., "Kinetics of two–site immunoradiometric ('sandwich') assays–II"., Immunochemistry, 1978, vol. 15, pp. 77–82.*
Labmedica Apr./May 1990.

* cited by examiner

Primary Examiner—Long V. Le
Assistant Examiner—Lisa V. Cook
(74) Attorney, Agent, or Firm—Jerome L. Jeffers (57) ABSTRACT

Disclosed is a method for determining the concentration of an analyte in a fluid test medium by use of an immunochromatographic test strip through which the test fluid can flow by capillarity. The test strip has at least two capture bands and optionally one or more collection bands which capture labeled anti-analyte antibody to provide a detectable signal. The signals from the label is quantitatively detected in each of the bands to provide a pattern of signals which is unique to the concentration of analyte in the test fluid. The pattern of signals are mathematically combined to create a monotonous dose-response curve to thereby factor out the high analyte hook effect which can be present in this type of assay.

11 Claims, 6 Drawing Sheets

METHOD FOR THE DETERMINATION OF ANALYTE CONCENTRATION IN A LATERAL FLOW SANDWICH IMMUNOASSAY EXHIBITING HIGH-DOSE HOOK EFFECT

BACKGROUND OF THE INVENTION

Immunochromatographic strip formats have become increasingly popular for quantitative and semi-quantitative assays which use visual detection schemes. This type of immunoassay involves the application of a liquid test sample suspected of containing an analyte to be detected to an application zone of an immunochromatographic test strip. The strip is comprised of a matrix material through which the fluid test medium and analyte suspended or dissolved therein can flow by capillarity from the application zone to a capture zone where a detectable signal, or the absence of such, reveals the presence of the analyte. Typically, the strip will include means for immunospecifically binding the analyte to be detected with its specific binding partner which bears the detectable label. In one such scheme, as disclosed in U.S. Pat. No. 4,446,232; the strip contains an enzyme labeled, mobile binding partner for the analyte which is in a zone of the strip downstream from the sample application zone. If analyte is present in the test sample, it will combine with its labeled binding partner to form a complex which will flow along the strip to a detection zone which contains a substrate for the enzyme label which is capable of providing a colored response in the presence of the enzyme label. The strip contains another zone in which analyte is immobilized, so that the labeled binding partner which does not combine with analyte, due to the absence of sufficient analyte in the sample, will be captured and thereby inhibited from reaching the detection zone. There have been published various modifications of this technique, all of which involve competitive specific binding systems in which the presence or absence of analyte in the test sample is determined by the detection or lack thereof of labeled binding partner in the capture zone.

An alternative to the above described immunometric assay which detects the free labeled antibody is the so called sandwich format in which the capture zone contains immobilized antibodies against an epitope of the analyte which is different than the epitope to which the labeled antibody is specific. In this format, there is formed a sandwich of the analyte between the immobilized and labeled antibodies and it is therefore an immunometric assay which detects the bound labeled antibody species. This type of immunostrip format works well in connection with the analysis of relatively low concentrations of analyte, but can be of limited utility in the analysis of fluids containing high analyte concentration. This adverse effect is caused by the presence of excessive free analyte in the sample that competes for binding with the immobilized antibody in the strip's capture band with the analyte which has become bound to the labeled antibody by interaction therewith in a portion of the strip upstream from the capture zone. This competition can result in less of the analyte/labeled antibody conjugate being captured by the capture antibody and consequently less signal being detected in the capture zone than would be in the case if there were less analyte in the test sample. A dose-response curve prepared using this type of test strip will show increasing signal with increasing analyte up to the point where the analyte concentration begins to block the interaction between the immobilized capture antibody and the analyte/labeled antibody complex. Beyond this point, increasing analyte in the test fluid results in a decrease in the signal, so that the dose-response curve indicates decreasing signal with increasing analyte. The slope of this sort of dose-response curve somewhat resembles a hook which accounts for this phenomena being known as the hook effect. Traditionally, when the hook effect is observed or suspected, the fluid sample is diluted to several dilutions to ensure the validity of the results. The high dose hook effect may not occur if sufficient labeled or capture antibody is present in the assay medium. A complete dose-response curve (low to high analyte concentration) is usually needed to verify the existence of this effect. Accordingly, sample dilution is generally carried out whenever there is reason to expect that the assay might exhibit the hook effect. It is an object of the present invention to provide a sandwich type assay method using an immunochromatographic strip whose efficacy is not affected by high analyte concentrations in the test sample and, accordingly, does not require sample dilution or reassaying of samples containing high analyte concentrations. This method involves providing a strip with at least two capture bands and optionally a collection band in which there is immobilized a binding partner for labeled antibody which will bind labeled antibody which has not formed a complex with analyte to thereby facilitate its capture in one of the capture bands. The collection band is optional since it is not needed for the assay method to work in the sandwich format. However, by using a strip which contains a collection band, each sample measurement will provide more information thereby improving the assay's sensitivity and/or precision.

In EP 0 462 376 $A_2$ there is disclosed a procedure in which signal at the capture site and conjugate collection site of an immunochromatographic strip are detected and the analyte concentration is determined by the intensity of the signal at the capture site relative to the signal at the recovery site. Also of interest in this regard is U.S. Pat. No. 5,569,608.

In co-pending application [Ser. No. 08/900,586] there is disclosed an assay using an immunochromatographic tographic strip having multiple capture and/or collection sites in which the signal from the detectable label in the capture zone(s) and collection zone(s) is determined whereupon a final response signal is determined using an algorithm and a number of signals which are chosen in a manner suited for a particular assay to provide a value for analyte concentration.

SUMMARY OF THE INVENTION

The present invention is a method for determining the concentration of an analyte in a fluid test medium. The method comprises the steps of:

a) Providing a strip of a porous material through which a test fluid suspected of containing the analyte can flow by capillarity; the strip has at least two distinct capture regions in which there are immobilized antibodies specific to a first epitope of the analyte. There are also provided antibodies specific to a second epitope of the analyte which bear a detectable label and are capable of flowing through the strip along with the fluid test medium upon applying it to the strip up stream from the first of the at least two distinct capture zones;

b) Applying the fluid test medium to the strip and allowing it to flow along the strip carrying labeled antibodies along with it to thereby contact the immobilized antibodies in the distinct capture regions. When sufficient analyte is present in the fluid test medium to partially block binding of the immobilized antibody with the first epitope of the analyte in at least the first distinct capture region with which the fluid test medium comes into contact as it flows along the strip, there is formed a sandwich of the immobilized antibody, the analyte and labeled antibody in the distinct capture regions through which the fluid test medium carries analyte the quantity of which sandwich is limited by the partial blocking of the immobilized antibody;

c) Detecting, in a quantitative manner, the signal emitted from the label on the labeled antibody in each of the distinct capture regions in which the sandwich has formed. This provides a pattern of signals which is unique to the concentration of analyte in the fluid test medium; and d) Mathematically combining the unique set of signals to create a monotonous dose-response curve to factor out the blocking of the binding between the immobilized antibody and the first epitope of the analyte.

DESCRIPTION OF THE INVENTION

The invention is practiced by first providing the test matrix through which the fluid test sample can flow by capillarity. Typically, the matrix will be in the form of a strip through which the test fluid flows horizontally. While the matrix could be assembled in a layered format through which the test fluid could flow vertically from top to bottom or vice-versa, the following discussion is focused on the preferred strip format.

The strip can be prepared from any matrix material through which the test fluid and an analyte contained therein can flow by capillarity and can be of a material which is capable of supporting non-bibulous lateral flow. This type of flow is described in U.S. Pat. No. 4,943,522 as liquid flow in which all of the dissolved or dispersed components of the liquid are carried through the matrix at substantially equal rates and with relatively unimpaired flow, as contrasted to preferential retention of one or more components as would be the case if the matrix material were capable of absorbing or imbibing one or more of the components. An example of such a material is the high density or ultra high molecular weight polyethylene sheet material obtainable from Porex Technologies. Equally suitable for use as the matrix from which the chromatographic strips can be fabricated are bibulous materials such as paper, nitrocellulose and nylon.

In a preferred embodiment of the present invention there is provided a test device comprising a strip of nitrocellulose having a region 2 (FIG. 1) which contains mobile specific binding partner for the analyte which bears a detectable label and can react with analyte present in the fluid test sample applied to wicking pad 1 to form an analyte/labeled binding partner complex upon applying the test sample to the wicking pad and allowing it to flow up the strip to region 2 where analyte in the test sample combines with labeled antibody specific to the analyte and flows to area 4 which contains two or more capture bands 3' which contain immobilized antibodies specific for an epitope of the analyte separate from that to which the labeled antibodies are specific to form an immobilized binding partner/analyte/labeled binding partner sandwich in one or more of capture bands. When the analyte level in the test fluid is low, the sandwich is formed in the first distinct capture region without any interference, and the signal from the labeled antibody can be read without additional steps. However, when excessive analyte is present, blocking of some binding sites on the immobilized antibody occurs thereby reducing sandwich formation in the first capture region. In this situation, unbound analyte-labeled antibody conjugate flows through the first capture region and is captured in the second capture region. When the analyte concentration is sufficiently high to block binding sites in the second capture region, capture of the analyte-labeled antibody conjugate takes place in a third or possible subsequent capture regions.

Figure 1:
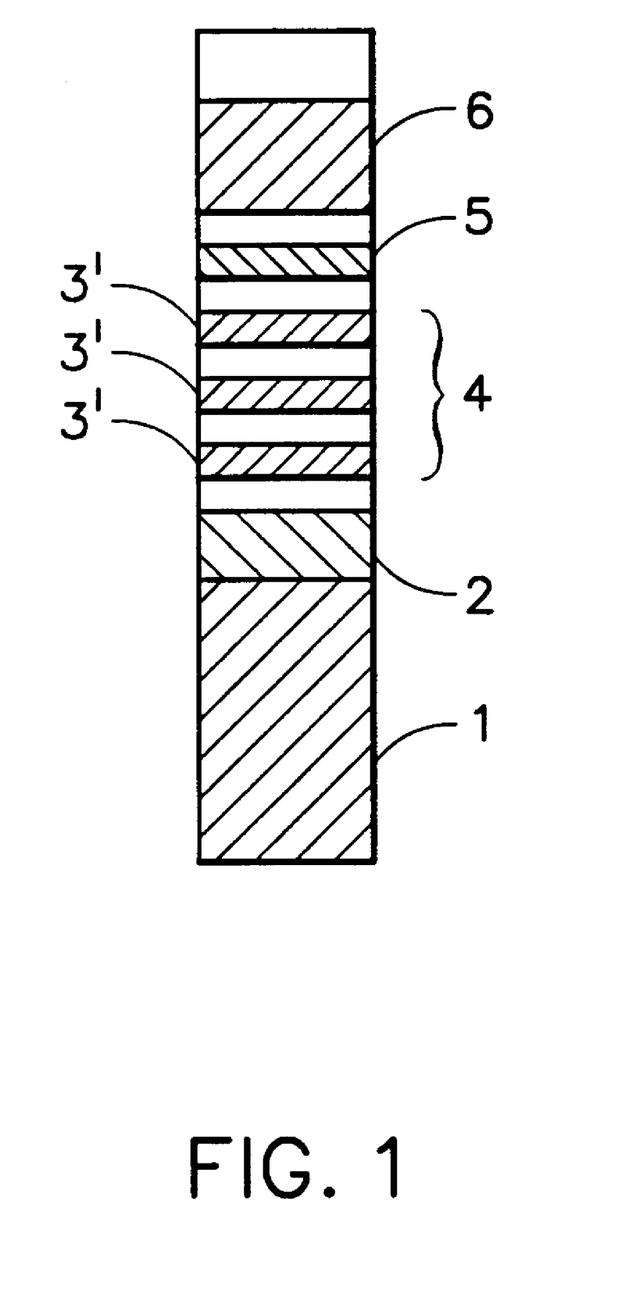
FIG. 1 is a representation of an assay device useful in the present invention.

The number of capture bands is generally determined by the analyte concentration range, the amount of immobilized antibody in each band and the levels of differentiation required. Theoretically, there is no limitation on the number of capture bands as long as they are needed and there is enough space available on the test strip. Typically, a maximum of 3 capture bands 3' will be incorporated into capture region 4 of the strip since this will provide enough capacity for most assays. The labeled anti-analyte antibody is typically added to region 2 but not in excess of that which is necessary to form conjugates with all of the analyte which would be expected to be present in the test sample. Excess labeled antibody/analyte conjugate is captured in the collection band of area 5 by a collection means for labeled antibody such as immobilized IgG or it may all bind to the capture bands at medium or high analyte concentration with no conjugate reaching the collection band. The collection band may function as an internal control for the assay or participate in the calculation of analyte concentration. In the latter embodiment, it is possible to have two or more collection bands on the strip for better analyte measurement to improve the assay performance. The strip may optionally contain a desiccated absorbant pad 6. This pad serves as a liquid sink to facilitate the capillary flow of test fluid through the strip. The desiccant in the pad enhances the process by effectively absorbing the liquid which reaches the top of the strip.

Upon development of the strip by application thereto of fluid test sample containing analyte, the signal produced by the label in each of the capture bands and optional collection bands is quantitatively detected, such as by use of a reflectance spectrometer, to obtain a pattern of signals which is unique to the concentration of analyte in the fluid test medium. This pattern of signals is then mathematically combined to create a monotonous (continuous increase with analyte concentration) dose-response curve. The curve is constructed to factor out the hook effect blocking of the binding between the immobilized antibody and the first epitope of the analyte which is accomplished by providing a one-to-one relationship between the assay response and the analyte concentration. The problem caused by the hook effect is that the same assay response can result from more than one analyte concentration. A monotonous dose-response curve alleviates this problem, so that unambiguous results can be obtained by a single sample measurement. An immunostrip for the detection of C-reactive protein (CRP) having multiple capture bands is disclosed in Labmedica, April/May 1990, but there is no suggestion that the signals from the capture bands be mathematically combined. It appears that the multiple capture bands in the strip described in this reference are used to indicate the analyte concentration level which is proportional to the number of visible bands on the strip. These multiple bands are not designed to measure the analyte in the range where hook effect occurs because this assay is based on sequential saturation of analyte-labeled antibody complex in the capture zones without the blocking of free analyte. This is in contrast to the mathematical treatment of the pattern of signals in the present invention. Unlike the immunostrip described in this reference, the present assay system is designed to directly measure the analyte concentration above the level where the hook effect occurs. The mathematical treatment of the signal patterns generated by the assay provides a unique revenus (a monotonous dose-response curve) to evaluate the analyte concentration beyond the limit imposed by the hook effect.

In a preferred method of practicing the present invention the antibody label is capable of reflecting light at a predetermined wavelength and there is provided a reflectance spectrometer having a detector of reflectance intensity with means for moving the developed strip and detector relative to each other such as a specimen table on which the strip is placed which can be moved laterally under the read head of the detector. This technique assists in providing accurate quantitation since the location of the strip relative to the detector can be under microprocessor control, so that the reflectance of the desired regions can be determined and then combined via the use of preprogrammed software to provide the monotonous dose-response curve. Other labels, such as radio isotopes and enzymes are suitable, since the only essential property of the label is that it be capable of being quantitatively detected.

In the preferred embodiment of the present invention in which the test strip contains 3 capture regions and a single collection region, the unique pattern of signals is combined by:

i) ratioing the signals of the second and third capture regions against the signal of the first capture region;

ii) multiplying the two ratios by numbers that are within the same range of magnitude as the signal from the collection region; and iii) subtracting the signal from the collection region from the sum of the two products derived in step ii.

The method of practicing the present invention is further illustrated by the following examples:

EXAMPLE I

Figure 3:
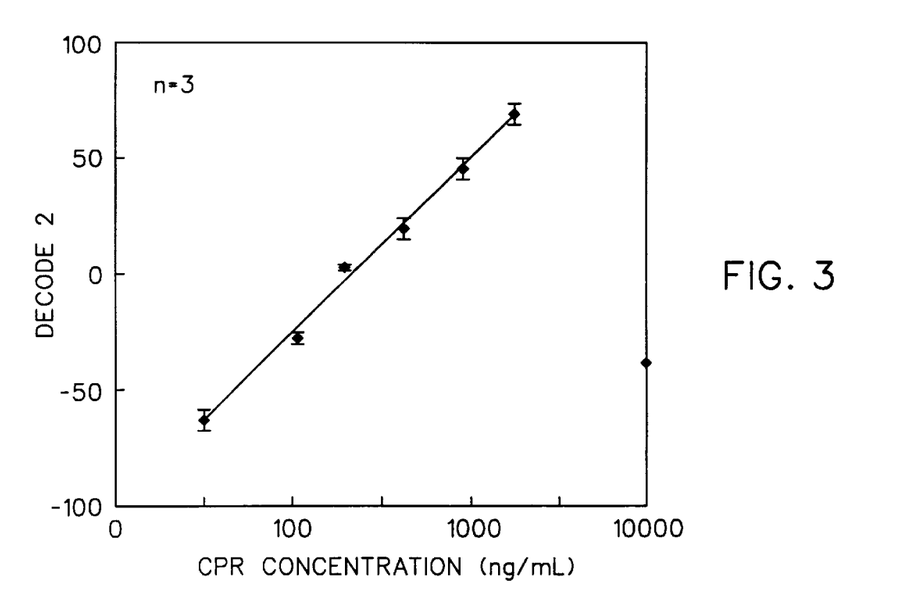
FIG. 3 represents a complete dose response curve of the reflectance change of an immunostrip having 3 capture bands and one collection band which have been combined according to the present invention.

The multiple band immunostrip format of the present invention was demonstrated using a lateral flow nitrocellulose strip containing three test bands of monoclonal mouse anti-C reactive protein (CRP) antibody and one control band of polyclonal donkey anti-goat antibody (IgG). The strip was prepared as follows:

The assay was performed by mixing CRP calibrator containing affinity purified CRP of known concentrations in buffer at pH 7.0 with an aqueous assay solution 0.2% (w/v) BSA; 0.05% (w/v) Triton X-100; 0.75% (w/v) glycine; 5.85% (w/v) NaCl and 0.2% (w/v) NaN$_3$ at pH 8.2 containing 0.04% (w/v) of a polyclonal goat anti-CRP antibody labeled with blue latex particles which was then pipetted onto a cassette containing the nitrocellulose strip. After five minutes the reflectance changes in the capture and collection bands were measured using a CLINITEK® 50 reflectance spectrometer. By using different decode calculations including $\Delta R$ where $\Delta R$=absolute background reflectance reading near the capture (test) or collection (control) bands minus absolute reflectance reading of the test or control band. Both reflectance readings were obtained 5 minutes after the start of the assay. Two dose response curves were obtained as set out in FIGS. 2 and 3. The first curve was derived from the reflectance change of the first test band, i.e. Decode 1=$\Delta R$ of first test band. The curve of FIG. 3 was generated by a method of data computation utilizing the change in reflectance from all 3 capture bands and the collection band (the assay response) to calculate the analyte concentration, i.e.:

$$\text{Decode 2}=100*T2/T1+50*T3/T1-CL$$

where:
$T1=\Delta R$ of first capture band
$T2=\Delta R$ of second capture band
$T3=\Delta R$ of third capture band
$CL=\Delta R$ of collection band The calculated decode values (overall assay responses) were plotted versus the known analyte concentrations and a dose-response curve (FIG. 3) was constructed by curve fitting. This curve is represented by the equation:

$$100*T2/T1+50*T3/T1-CL=31.005*\text{Ln(Analyte concentration)}-170.29$$

By solving this equation with assay responses obtained from the capture and collection bands using test fluid containing unknown concentrations of analyte, the unknown analyte concentration was calculated as:

$$\text{Analyte concentration}=\text{Exp}[(100*T2/T1+50*T3/T1-CL+170.29)/31.005]$$

Figure 2:
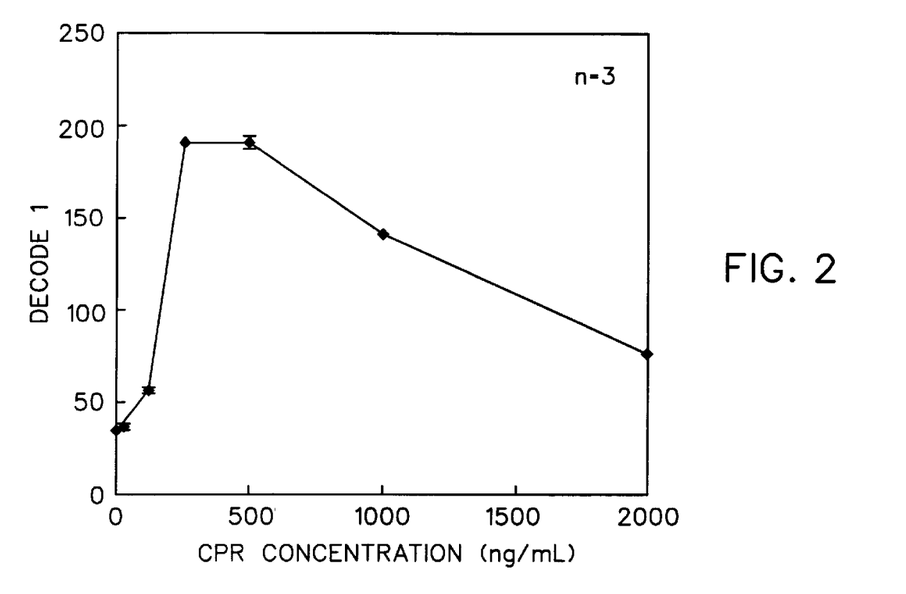
FIG. 2 is a dose response curve of the reflectance change of an immunostrip having only one capture band.

As shown by the first dose response curve of FIG. 2, the dynamic range of the assay in which only a single band is read is limited by the high dose hook effect, i.e. the analyte concentration above a certain threshold cannot be measured without sample dilution because of a decrease in the response signal. In contrast to the single band test, the multiple band assay gives more than one result per test and displays a unique pattern of band signals for each analyte concentration level. These patterns can be used directly for assessment or represented numerically, such as in the dose response curve of FIG. 3, for quantitative or semi-quantitative evaluation. Dynamic range is the range between the maximum and minimum assay responses. In FIG. 3, the dynamic range is approximately –60–70.

EXAMPLE II

In addition to analyte measurement with a single dose-response curve, the multiple band assay provides the option of multi-curve analyte calculation. This calculation method divides the entire analyte concentration range into a few sections which are governed by dose-response curves derived from various signal combinations. It is designed to utilize the most sensitive portion of each dose-response curve in a specified concentration region so that any level of analyte (high, medium or low) can be estimated with minimum error. An algorithm based on the signal from each band is used to direct each obtained assay response to the correct concentration region for data processing.

Figure 6:
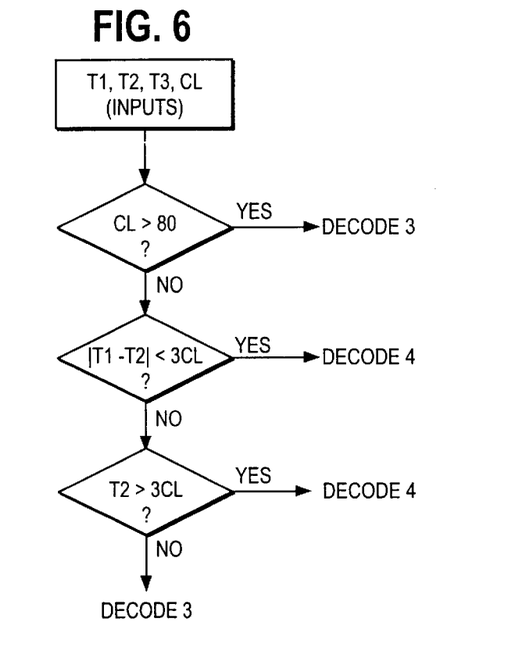
FIG. 6 represents a multi-curve analyte calculation according to the present invention.

An example of a multi-curve analyte calculation using two dose-response curves is illustrated by the algorithm set out in FIG. 6:

This algorithm was derived empirically by comparing the experimental data. The algorithm is designed to demonstrate how a multicurve analyte calculation can be carried out in accordance with the present invention. The decision routine, including the step CL>80?, |T1—T2|<3CL?, T2>3CL?, is one method of determining whether the analyte concentration of the test sample was above or below 250 ng/mL which was the borderline between the two regions governed by the dose-response curves shown in FIGS. 4 and 5. The decodes represent values derived from the reflectance changes of capture and collection bands to calculate the analyte concentration based on a dose response curve. Decode is a number representing the reflectance of color from the reagent as measured by the CLINITEK® instrument.

Figure 4:
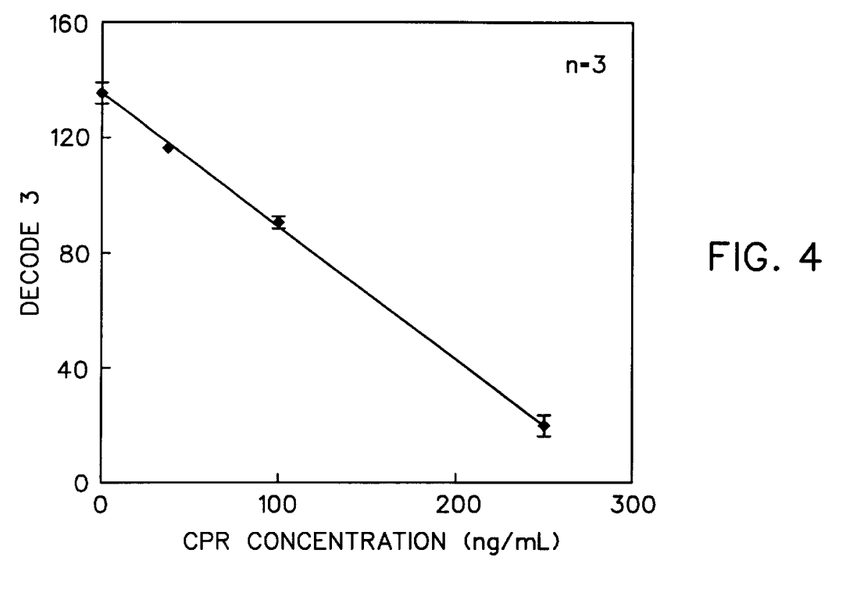
FIGS. 4 and 5 are partial dose-response curves of the reflectance change of an immunostrip having 3 capture bands and one collection band which have been combined by multiple mathematical methods.

This experiment was also carried out using calibrators of known analyte concentrations. The assay responses were divided into two groups based on their corresponding analyte concentrations. For the group having low analyte concentrations (0~250 mg/mL), the assay responses were mathematically combined by the defined decode 3 equation decode 3=Cl. The dose response curve for decode 3=CL is set out in FIG. 4. This equation includes only the response from the collection band because the capture bands did not exhibit a significant level of differentiation at the low end of the concentration range. The decode values were then plotted against the known analyte concentrations and used to generate a dose-response curve by curve fitting (FIG. 4). The mathematical equation for the curve was represented by the equation:

$$\text{Decode 3} = -0.4675 * (\text{Analyte concentration}) + 134.08$$

Figure 5:
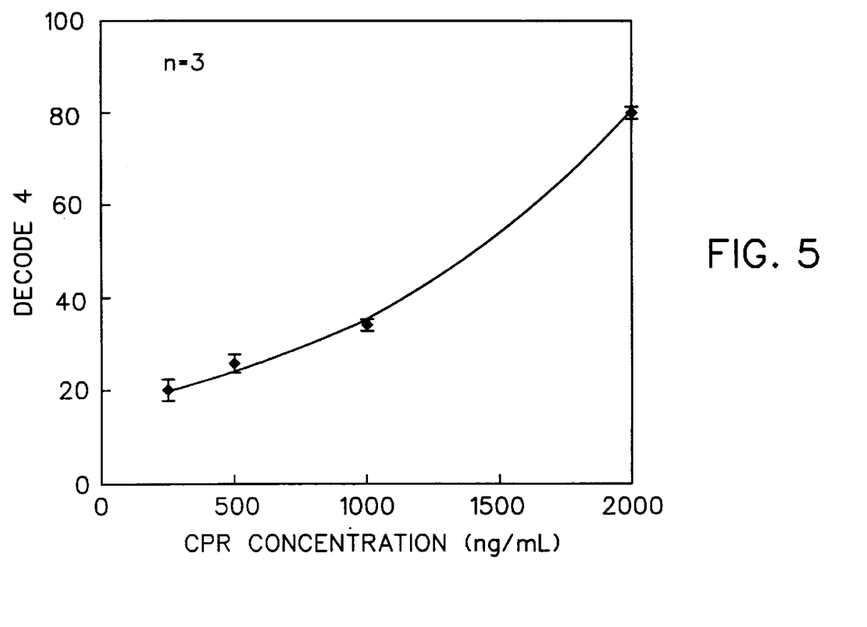

The dose response curve for decode 4=T1/CL+10* T2/T1+100*T3/T1 is set out in FIG. 5. The result and decode values were plotted against the known analyte concentrations to obtain a dose-response curve by curve fitting. Several signal combinations (decode calculations) were then used to generate a group of dose response curves (such as FIGS. 4 and 5) that are sensitive (significant change in assay response as the analyte concentration varies) in different analyte concentration regions.

$$\text{Decode 4} = 16.302 * \text{Exp}[0.0008 * (\text{Analyte concentration})]$$

which was combined with the defined Decode 4 equation to give $$T1/CL + 10 * T2/T1 + 100 * T3/T1 = 16.302 * \text{Exp}[0.0008 * (\text{Analyte concentration})]$$

This equation was then transformed into $$\text{Analyte concentration} = \text{Ln}[(T1/CL + 10 * T2/T1 + 100 * T3/T1)/16.302]/0.0008$$

which was used to determine the unknown analyte concentration of test sample.

When a sample is assayed by the multiple-band immunoformat, the reflectance change of each individual band is used to estimate the analyte concentration. This is done by using a screening algorithm (developed empirically or theoretically) which suggests the proper dose-response curve (the one that is most sensitive in the estimated concentration region) in the established group for analyte evaluation. The established group is the group of dose-response curves described in the previous paragraph which are generated by various signal combinations (decode calculations) and are sensitive in different analyte concentration regions. In the present example, the established group is composed of the dose-response curves shown in FIGS. 4 and 5. The screening process is accomplished by three sequential decision steps. In the first step, the reflectance change of the collection band is evaluated. If it is greater than 80, the analyte concentration centration is calculated using the Decode 3 equation and the dose-response curve shown in FIG. 4. Otherwise, the screening process continues to the second step in which the absolute value of the difference between the reflectance changes of the first and the second capture bands is compared with the product of 3× the reflectance change of the capture band. If the former is less than the latter (|T1−T2|,3CL), the analyte concentration is by the decode 4 equation and the dose-response curve shown in FIG. 5. For other cases (|T1−T2|≧3CL), the third screening step is performed by examining whether the reflectance change of the second capture band is greater than the produce of 3× the reflectance change of the collection band. If yes (T2>3CL), the mathematical method involving the decode 4 equation is used for analyte estimation. Elsewise, the decode 3 equation and its corresponding dose-response curve are employed. The advantage of this method is to reduce error in analyte measurement by using sensitive dose response curves across the entire analyte concentration range. A single band immunoformat is unable to provide this advantage because multiple dose response curves cannot be created.

EXAMPLE III

Figure 7:
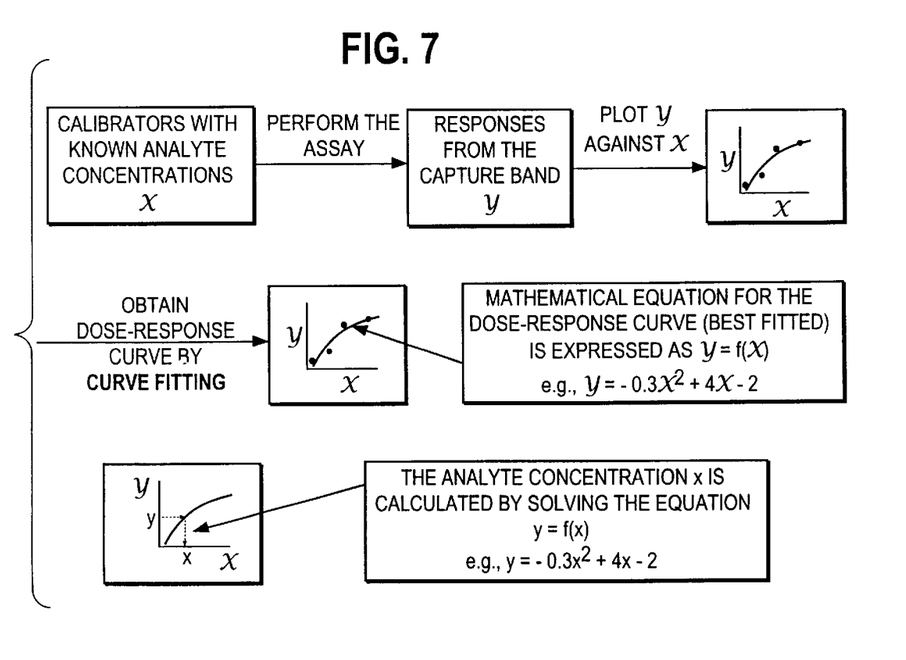
FIGS. 7, 8 and 9 demonstrate how to establish a typical dose response curve for use in the present invention.

This is a generalized example in which the sandwich assay for an analyte is carried out using an immunoformat having a single capture band and using an immunoformat with multiple capture bands. For a typical sandwich immunoformat with a single capture band, the dose-response curve is established as indicated by FIG. 7:
where the equation Y=f(X) is the best fitted dose-response curve obtained by curve fitting.

Figure 8:
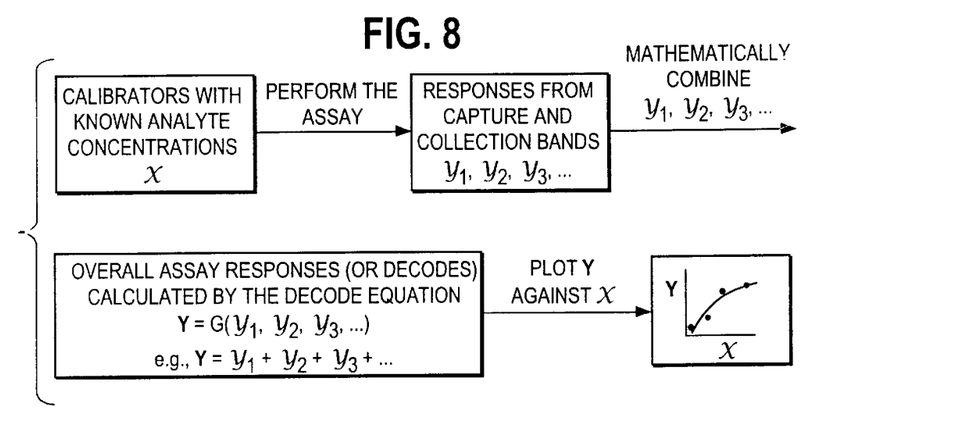
Figure 9:
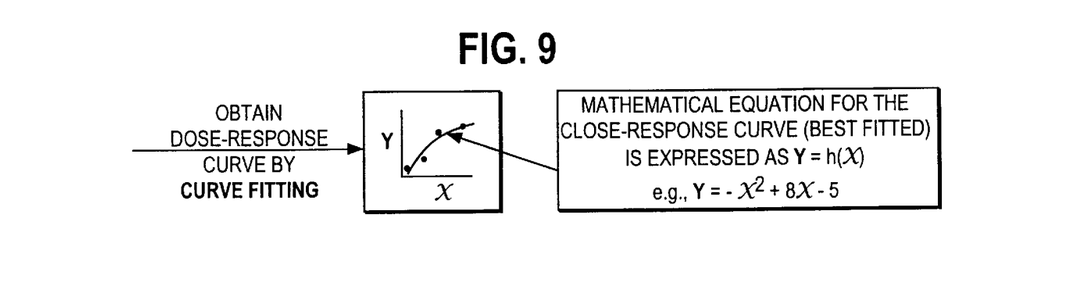

The present invention involves the use of a sandwich immunoformat with multiple capture bands. More than one dose response curve (one for each capture band) is prepared by performing the assay with calibrators of known analyte concentration. The analyte concentration of the test sample is calculated by simultaneously solving multiple mathematical equations, each of which represents an individual dose-response curve. One way to simplify this complex procedure is to mathematically combine the responses of capture and collection bands by a defined equation (referred to herein as a decode equation) to form an overall assay response (referred to herein as decode) which is similar to that of an immunoformat with a single capture band. The data processing steps are illustrated as follows:

1) Establishment of Dose-response Curve is illustrated by FIG. 8
where g is a mathematical function describing how $Y_1$, $Y_2$, $Y_3$ . . . are combined, and FIG. 9
where h=the best fitted dose-response curve which is obtained by curve fitting.

Figure 10:
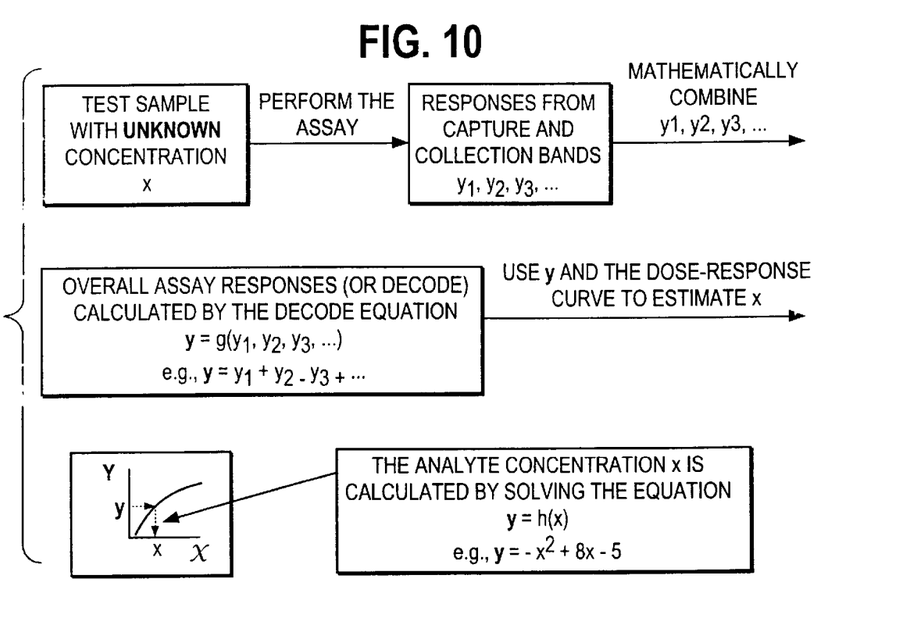
FIGS. 10 and 11 illustrate the calculation of unknown analyte concentration.

2) Calculation of Unknown Analyte Concentration is illustrated by FIG. 10

Figure 11:
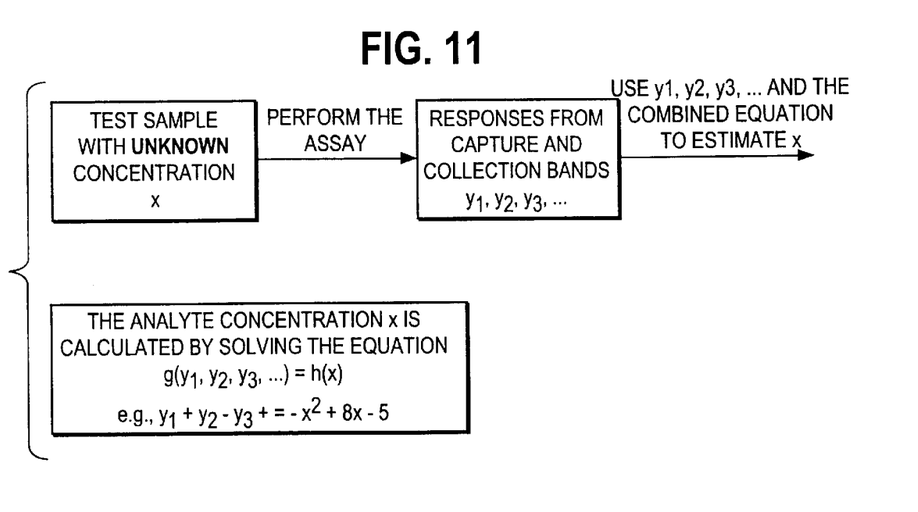

The decode equation $y = g(y_1, y_2, y_3 \ldots )$ and the dose-response curve equation $y = h(x)$ can be combined to give:

$g(y_1, y_2, y_3 \ldots ) = h(x)$ and the calculation of unknown analyte concentration is illustrated by FIG. 11:

These data processing steps, including the establishment of the dose-response curve and calculation of the unknown analyte concentration, were followed in both Examples I and II.

What is claimed is:

1. A method for determining the concentration of an analyte in a fluid test medium susceptible of exhibiting a high-dose hook effect, which comprises:

a) providing a strip of a test matrix through which the test fluid suspected of containing the analyte can flow by capillarity which strip has at least two distinct capture regions in which are immobilized antibodies specific to a first epitope of the analyte and labeled antibodies whose labels provide a detectable signal and which antibodies specific to a second epitope of the analyte which in or applied to the strip upstream from the capture regions and which are able to flow through the strip along with the fluid test medium upon its application to the strip;

b) applying the fluid test medium to the strip and allowing it to flow along the strip carrying the labeled antibodies with it to thereby contact the immobilized antibodies in the distinct capture regions and, when sufficient analyte is present in the fluid test medium to partially block binding of the immobilized antibody with the first epitope of the analyte in at least the first distinct capture region with which the fluid comes into contact as it flows along the strip to form a sandwich of the immobilized antibody, analyte and labeled antibody in the distinct capture regions through which the fluid test medium carries analyte the quantity of which sandwich formation is limited by the partial blocking of the immobilized antibody;

c) quantitatively detecting the signal from the label on the labeled antibody in each of the distinct capture regions in which the sandwich has formed to obtain a pattern of signals which pattern is unique to the concentration of analyte in the fluid test medium; and d) mathematically combining the unique pattern of signals to create a monotonous dose-response curve to factor out the blocking of the binding between the immobilized antibody and the first epitope of the analyte;

e) determining the concentration of analyte by determining where the response for a given fluid test medium falls on the dose-response curve.

2. The method of claim 1 wherein the strip has at least one collection region in which there is immobilized a collection means for the labeled antibody.

3. The method of claim 2 wherein the strip has 3 capture regions and one collection region and the unique pattern of signals is combined by:

i) ratioing the signals of the second and third capture regions against the signal of the first capture region;

ii) multiplying the two ratios by numbers that are in the same range of magnitude as the signal of the collection region; and iii) subtracting the signal of the collection region from the sum of the two products obtained in step ii.

4. The method of claim 2 wherein the collection means is IgG.

5. The method of claim 2 wherein the labeled antibody is labeled with a material capable of reflecting light at a predetermined wavelength and the signal from the labeled antibody is quantitatively detected by measuring the change in reflectance ($\Delta R$) from the capture and collection regions by means of a reflectance spectrometer after application of the test sample.

6. The method of claim 5 wherein there are 3 capture regions and 1 collection region on the strip and the analyte concentration is determined by solving the equation:

$$\text{Analyte concentration} = e(100*T2/T1 + 50*T3/T1 - CL) + 170.29/31.005$$

where:

$T1 = \Delta R$ of first capture region $T2 = \Delta R$ of second capture region $T3 = \Delta R$ of third capture region $CL = \Delta R$ of collection region.

7. The method of claim 5 wherein there are 3 capture regions and 1 collection region on the strip and the analyte concentration is determined by:

a) solving the equation:

$$\text{Decode} = 100*T2/T1 + 50*T3/T1 - CL$$

where:

$T1 = \Delta R$ of first capture region $T2 = \Delta R$ of second capture region $T3 = \Delta R$ of third capture region $CL = \Delta R$ of collection region to determine a decode value, and b) plotting the decode value against analyte concentration on a dose response curve to obtain the analyte concentration.

8. The method of claim 1 wherein the analyte concentration is determined by a multi-curve calculation in which the entire analyte concentration range is divided into sections which are governed by dose-response curves derived from various signal combinations.

9. The method of claim 1 wherein the fluid test medium comprises urine.

10. A method for determining the concentration of an analyte in a fluid test medium susceptible of exhibiting a high-dose hook effect, which comprises:

a) providing a strip of a test matrix through which the fluid test medium suspected of containing the analyte can flow and which strip has at least two distinct capture bands in which are immobilized antibodies specific to a first epitope of the analyte and which strip bears labeled antibodies whose labels provide a detectable signal and upstream from the capture bands which are specific to a second epitope of the analyte and which are able to flow through the strip along with the fluid test medium upon its application to the strip;

b) applying the fluid test medium to the strip and allowing it to flow along the strip and carry the labeled antibodies with it to thereby contact the immobilized antibodies in the capture bands and, when sufficient analyte is present in the fluid test medium to partially block binding of the immobilized antibody with the first epitope of the analyte in the first capture band with which the fluid test medium comes into contact as it flows through the strip to form a sandwich of the immobilized antibody, analyte and labeled antibody in the distinct capture hands through which the fluid test medium carries the analyte, the quantity of which sandwich formation is limited by the partial blocking of the immobilized antibody;

c) quantitatively detecting the signal from the labeled antibody in each of the distinct capture bands in which the sandwich has formed to obtain a pattern of signals, which pattern is unique to the concentration of analyte in the fluid test medium;

d) mathematically combining the signals from each of the capture bands into the expression $Y = g(Y_1, Y_2, Y_3 \ldots)$ where Y is the overall assay response, g is a mathematical function describing how $Y_1, Y_2$ and $Y_3 \ldots$ are combined and each of $Y_1, Y_2, Y_3 \ldots$ are individual responses from each of the individual capture bands;

e) providing a plot of Y against X where X is a calibrator value for known concentrations of analyte and preparing a dose response curve by solving the equation Y=h(X) where h=the best fitted dose-response curve which is obtained by curve fitting to obtain the best fitted dose response curve thereby creating a monotonous dose-response curve to factor out the blocking between the antibody and the analyte; and f) calculating the concentration of analyte in the fluid test medium by mathematically combining the results from the capture bands to obtain an overall assay response, $Y=Y_1+Y_2 \ldots$ and calculating the analyte concentration X by solving the equation Y=h(X).

11. The method of claim 10 wherein the strip contains two capture bands and a single collection region in which there is immobilized a collection means for the labeled antibody wherein the signal from any labeled antibody is also quantitatively detected and Y is determined by solving the equation $Y=y_1+y_2-y_3$ where $y_1$ and $y_2$ are the signals from the two capture bands and $y_3$ is the signal from the collection region.

* * * * *